(12) United States Patent
Bui et al.

(10) Patent No.: US 8,999,304 B2
(45) Date of Patent: Apr. 7, 2015

(54) LONG-WEARING NON-AQUEOUS STRUCTURED COLOR COSMETIC

(75) Inventors: Hy Si Bui, Piscataway, NJ (US); Mohamed Kanji, Edison, NJ (US); Chunhua Li, Scotch Plains, NJ (US)

(73) Assignee: L'Oréal (FR)

( * ) Notice: Subject to any disclaimer, the term of this patent is extended or adjusted under 35 U.S.C. 154(b) by 0 days.

(21) Appl. No.: 13/583,676

(22) PCT Filed: Mar. 10, 2011

(86) PCT No.: PCT/US2011/027887
§ 371 (c)(1),
(2), (4) Date: Sep. 10, 2012

(87) PCT Pub. No.: WO2011/112804
PCT Pub. Date: Sep. 15, 2011

(65) Prior Publication Data
US 2013/0004446 A1    Jan. 3, 2013

Related U.S. Application Data

(60) Provisional application No. 61/312,569, filed on Mar. 10, 2010, provisional application No. 61/312,532, filed on Mar. 10, 2010.

(51) Int. Cl.
| | |
|---|---|
| A61K 8/00 | (2006.01) |
| A61K 8/18 | (2006.01) |
| A61Q 1/02 | (2006.01) |
| A61K 8/04 | (2006.01) |
| A61K 8/34 | (2006.01) |
| A61K 8/44 | (2006.01) |
| A61K 8/891 | (2006.01) |
| A61Q 1/10 | (2006.01) |

(52) U.S. Cl.
CPC ........... *A61K 8/042* (2013.01); *A61K 8/345* (2013.01); *A61K 8/44* (2013.01); *A61K 8/891* (2013.01); *A61Q 1/02* (2013.01); *A61Q 1/10* (2013.01); *A61K 2800/30* (2013.01)

(58) Field of Classification Search
None
See application file for complete search history.

(56) References Cited

U.S. PATENT DOCUMENTS

| | | |
|---|---|---|
| 4,291,018 A | 9/1981 | Oeda et al. |
| 5,424,070 A | 6/1995 | Kasat et al. |
| 5,716,604 A | 2/1998 | Coe et al. |
| 7,758,848 B2 * | 7/2010 | Lu et al. ............ 424/64 |
| 2002/0127192 A1 | 9/2002 | Murphy et al. |
| 2002/0159961 A1 | 10/2002 | Yamato et al. |
| 2004/0170586 A1 | 9/2004 | Ferrari et al. |
| 2004/0229984 A1 | 11/2004 | Yamato et al. |
| 2005/0220728 A1 | 10/2005 | Kanji et al. |
| 2006/0110345 A1 * | 5/2006 | Lu et al. ............ 424/64 |
| 2006/0134037 A1 | 6/2006 | Cropper et al. |
| 2007/0128233 A1 | 6/2007 | Lu et al. |
| 2007/0243151 A1 | 10/2007 | Healy |
| 2007/0258923 A1 | 11/2007 | Bui et al. |
| 2008/0057011 A1 | 3/2008 | Ferrari |
| 2008/0102048 A1 | 5/2008 | McDermott |
| 2009/0280076 A1 * | 11/2009 | Yoshida et al. .......... 424/59 |
| 2009/0280077 A1 * | 11/2009 | Yoshida et al. .......... 424/59 |
| 2009/0317345 A1 | 12/2009 | Joshi et al. |
| 2010/0203097 A1 * | 8/2010 | Tanaka ............ 424/401 |
| 2012/0045493 A1 * | 2/2012 | Popoff et al. .......... 424/401 |

OTHER PUBLICATIONS

International Search Report Application No. PCT/US2011/027887, dated Nov. 25, 2011.
International Search Report Application No. PCT/US2011/027866, dated Nov. 24, 2011.
International Search Report Application No. PCT/US2011/027873, dated Nov. 24, 2011.
International Search Report Application No. PCT/US2011/027877, dated Nov. 25, 2011.
International Search Report Application No. PCT/US2011/027880, dated Nov. 25, 2011.

* cited by examiner

*Primary Examiner* — Robert A Wax
*Assistant Examiner* — Olga V Tcherkasskaya
(74) *Attorney, Agent, or Firm* — Lerner, David, Littenberg, Krumholz & Mentlik, LLP

(57) ABSTRACT

Disclosed are non-aqueous compositions capable of forming a gel structure, containing: (a) a low molecular mass N-acyl glutamic acid diamide having a straight-chain alkyl group; (b) a low molecular mass N-acyl glutamic acid diamide having a branched-chain alkyl group; (c) at least one gel-promoting solvent; (d) at least one film former; (e) at least one volatile solvent capable of solubilizing the film former; and (f) at least one colorant; and (g) a polyorganosiloxane-containing polymer, wherein the composition has a hardness value ranging from about 30 to about 300 gf, a melting point of about 500 C or higher, does not require use of wax as a structuring agent. Methods of making and using the compositions are also disclosed.

11 Claims, No Drawings

LONG-WEARING NON-AQUEOUS STRUCTURED COLOR COSMETIC

CROSS-REFERENCE TO RELATED APPLICATIONS

The present application is a national phase entry under 35 U.S.C. § 371 of International Application No. PCT/US2011/027887 filed Mar. 10, 2011, published in English, which claims priority from U.S. Provisional Patent Application Nos. 61/312,569, and 61/312,532, both filed Mar. 10, 2010, all of which are incorporated herein by reference.

FIELD OF THE INVENTION

The present invention relates, in general, to a non-aqueous, structured composition. More particularly, the present invention relates to a non-aqueous, structured, composition which elegantly deposits an active ingredient, such as a colorant, onto a targeted substrate, is long-wearing, possesses good storage stability, particularly with respect to variations in temperature, has good payoff and does not require the use of wax as a structuring agent.

BACKGROUND OF THE INVENTION

Conventional structured compositions typically employ various types of waxes as structuring agents in order to form user-friendly products having good pay-off (a term used to describe both the amount of product applied onto a target substrate, as well as, the way the product distributes onto the substrate), and stability properties, particularly with respect to temperature stability. The problem with wax-based stick compositions is that they possess an undesirable waxy feel and poor long-wear properties.

Attempts have been made to formulate structured gel compositions in the absence of wax. For example, various types of polyamides have been commercialized as gellators/structuring agents in order to form solid compositions. Similarly, various glutamides, as well as various types of polyurethanes have also been commercialized in order to form solid, preferably clear, compositions. Such attempts, however, while successful at making solid compositions, yielded numerous technical problems.

One of the technical problems associated with the above-referenced, commercial wax-free compositions involves their stability when exposed to elevated temperatures. It is imperative, from a practical point of view, that such compositions be able to withstand fluctuations in temperature during conventional storage conditions without their becoming too soft, thereby negatively impacting their use profile. In order to avoid such stability issues, the composition must possess a certain melting point profile.

Another technical problem relates to the way in which the composition is deposited onto a target substrate, also referred to as "pay-off". Poor pay-off, defined as too much deposit, too little deposit, or lack of uniformity of deposit, is primarily associated with the hardness/elasticity of the structured composition. Thus, in order to avoid such deposit issues, particularly with respect to color deposit, it is necessary that the composition possess certain hardness/elasticity properties.

It is therefore an object of the present invention to provide a non-aqueous, structured composition that does not suffer from the aforementioned technical problems.

BRIEF SUMMARY OF THE INVENTION

A first aspect of the present invention is directed to a non-aqueous composition that is capable of forming a gel structure, (e.g., a soft gel or a more structured, hard or molded gel such as a gel stick), containing:

(a) a low molecular mass N-acyl glutamic acid diamide having a straight-chain alkyl group;
(b) a low molecular mass N-acyl glutamic acid diamide having a branched-chain alkyl group;
(c) at least one gel-promoting solvent;
(d) at least one film former;
(e) at least one volatile solvent capable of solubilizing the film former;
(f) at least one colorant, and
(g) at least one polyorganosiloxane-containing polymer, wherein the composition has a hardness value ranging from about 30 to about 300 gramforce (gf), a melting point of about 50° C. or higher, and does not require use of wax as a structuring agent (e.g., is wax-free).

A second aspect of the present invention is directed to a process for making a non-aqueous, structured, gel-form composition comprising:

(a) providing a low molecular mass N-acyl glutamic acid diamide having a straight-chain alkyl group;
(b) providing a low molecular mass N-acyl glutamic acid diamide having a branched-chain alkyl group;
(c) providing at least one gel-promoting solvent;
(d) providing at least one film former;
(e) providing at least one volatile solvent capable of solubilizing the film former;
(f) providing at least one colorant; and
(g) providing at least one polyorganosiloxane-containing polymer;
(h) mixing (a)-(g), at a temperature generally ranging from about 80° C. to about 125° C.; and
(i) cooling the heated composition to form the non-aqueous composition, wherein the composition has a hardness value ranging from about 30 to about 300 gf, a melting point of about 50° C. or higher, and does not require use of wax as a structuring agent (e.g., is wax-free). In some embodiments, the temperature ranges from about 80-100° C., and in other embodiments from about 90-125° C. Preparing the compositions at these temperatures minimizes both the cost, and degree of manufacturing difficulty.

In some embodiments, the process for making the non-aqueous composition comprises: a) providing a first composition, comprising: i) a low molecular mass N-acyl glutamic acid diamide having a straight-chain alkyl group; ii) a low molecular mass N-acyl glutamic acid diamide having a branched-chain alkyl group; iii) at least one gel-promoting solvent; b) providing a second composition, comprising: (i) at least one film former; ii) at least one volatile solvent; iii) at least one colorant; and iv) at least one polyorganosiloxane-containing polymer; c) mixing (a) and (b) at a temperature of from about 80° C. to about 125° C., to form a heated composition; and d) cooling the heated composition to form the non-aqueous composition.

DETAILED DESCRIPTION OF THE INVENTION

Other than in the operating examples, or where otherwise indicated, all numbers expressing quantities of ingredients and/or reaction conditions are to be understood as being modified in all instances by the term "about" which as used herein refers to ±10-±15% of the referenced value As used herein, "structured" means gelled and/or rigidified.

Low Molecular Mass Organogellators

It has surprisingly been discovered by the inventor that the combination of at least one N-acyl glutamic acid diamide having a straight-chain alkyl group, such as dibutyl lauroyl glutamide, with at least one N-acyl glutamic acid diamide having a branched-chain alkyl group, such as dibutyl ethylhexanoyl glutamide, facilitates the formation of a gel carrier composition having optimal physical properties, and which are also long wearing, have good pay-off, are stable under conventional storage conditions and do not require use of a wax as a structuring agent (e.g., they are wax-free).

The composition of the present invention is formed by combining a first low molecular mass N-acyl glutamic acid diamide, or derivative thereof, having a straight-chain alkyl group, with a second low molecular mass N-acyl glutamic acid diamide, or derivative thereof, having a branched-chain alkyl group, and at least one solvent capable of forming hydrogen bonds with the low molecular mass organogellators. The term "low molecular mass" as used herein refers to a molecular mass from greater than zero up to about 2,000 daltons.

The dibutyl lauroyl glutamide is present in an amount generally ranging from about 0.1 to about 10% by weight, such as from about 0.5 to about 5% by weight, and from about 1 to about 3% by weight, all weights being based on the total weight of the composition. For purposes of making the compositions of the present invention that contain a colorant and a polyorganosiloxane-containing polymer, the dibutyl lauroyl glutamide is employed in an amount generally ranging from about 0.1 to about 50% by weight, such as from about 0.2 to about 40% by weight, and from about 0.3 to about 30% by weight, all weights being based on the total weight of the first composition.

The dibutyl ethylhexanoyl glutamide is present in an amount generally ranging from about 0.1 to about 10% by weight, such as from about 0.5 to about 5% by weight, and from about 1 to about 3% by weight, all weights being based on the total weight of the composition. For purposes of making the compositions of the present invention that contain a colorant and a polyorganosiloxane-containing polymer, the dibutyl ethylhexanoyl glutamide is employed in an amount generally ranging from about 0.1 to about 50% by weight, such as from about 0.2 to about 40% by weight, and from about 0.3 to about 30% by weight, all weights being based on the total weight of the first composition.

The dibutyl lauroyl glutamide is commercially available as GP-1 and the dibutyl ethylhexanoyl glutamide is commercially available as EB-21, both available from Ajinomoto of Fort Lee, N.J.

In a preferred embodiment, the first low molecular mass N-acyl glutamic acid diamide and second low molecular mass N-acyl glutamic acid diamide are employed in a ratio by weight of from about 1:1 to about 3:1, and preferably from about 1.5:1.

Gel-Promoting Solvent

The low molecular mass organogellators of the present invention are solubilized in a solvent capable of promoting gel formation. Polar and non-polar solvents may be utilized. Solvents capable of promoting gel formation include, for example, alcohols, monoalcohols, dialcohols, acids, esters, and the like.

It is preferred to utilize a polar solvent. Preferred polar solvents include, but are not limited to, C2-C5 glycols, such as propylene glycol, butylene glycol and pentylene glycol. These solvents are believed to promote gel formation by inhibiting intercalation (intramolecular bonding) in the glutamide molecules. Other preferred solvents include, for example, octododecanol, isostearyl alcohol, and the like. Yet other preferred solvents include substituted hydrocarbyl siloxanes, as disclosed, for example, in U.S. Patent Application Publication 2004/0223936 A1. They are believed to promote hydrogen bond formation between molecules of the glutamides. One exemplary substituted hydrocarbyl siloxane is CARBINOL FLUID, bis-hydroxyethoxypropyl dimethicone, which is a hydrocarbyl functional organopolysiloxane having the formula, $R^1Me_2SiO(Me_2SiO)_xSiMe_2R^1$ where $R^1$ is $-(CH_2)_3OCH_2CH_2OH$, and x is such to provide the product with a viscosity of about 50 cS ($mm_2/s$) at 23° C. The solvents listed herein may be used individually or in combination of two or more.

It is preferred that the solvents be capable of dissolving said organogellators at a temperature of from about 80° C. to about 100° C.

The at least one gel-promoting solvent will typically be employed in an amount of from about 3 to about 20% by weight, such as from about 5 to about 15% by weight, and from about 7 to about 10% by weight, all weights being based on the total weight of the composition. For purposes of making the compositions, the gel-promoting solvent will typically be employed in an amount of from about 10 to about 99% by weight, such as from about 20 to about 90% by weight, and from about 30 to about 80% by weight, all weights being based on the total weight of the first composition.

Film-Forming Polymer

"Film-forming polymer" as used herein means a polymer that, after dissolution in at least one solvent (such as, for example, an organic solvent), leaves a film on the substrate to which it is applied, for example, once the at least one solvent evaporates, absorbs and/or dissipates on the substrate.

The at least one film-forming polymer may be chosen from silicone film formers, vinyl and acrylic polymers, polyurethanes, polyesters, alkyl resins, epoxy ester resins, and cellulosic polymers.

A particularly preferred class of film-forming polymer are silicone film formers and, even more particularly, silsesquioxanes.

Silsesquioxane resins are a specific form of silicone resins. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure 1:

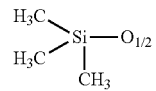

At least one of the methyl groups of the M unit may be replaced by another group, e.g., to give a unit with formula $[R(CH_3)_2]SiO_{1/2}$, as represented in the following structure 2:

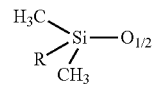

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as Structure 3:

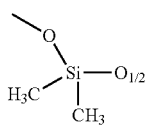

Here again, at least one of the methyl groups of the D unit may be replaced by another group, e.g., to give a unit with formula $R_aR_bSiO_{2/2}$, $RCH_3SiO_{2/2}$ or wherein $R_a$ and $R_b$ may be chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol T denotes the trifunctional unit, $CH_3SiO_{3/2}$ and can be represented as Structure 4:

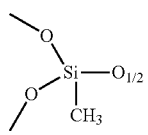

Here again, the methyl group may be replaced by another group, e.g., to give a unit with formula $RSiO_{3/2}$, wherein R may be chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, phenyl groups, alkoxy groups, wherein the groups other than methyl groups may be further substituted.

Similarly, the symbol Q denotes the tetrafunctional unit, $SiO_{4/2}$ wherein all four oxygens bonded to the silicone atom are bonded to the rest of the polymer.

When the film forming resin is made up predominantly of trifunctional units or T units, it is generally called a silsesquioxane resin. If it is made up primarily of repeating units as depicted in Structure 4, it is called a polymethylsilsesquioxane. A non-limiting example of the at least one polymethylsilsesquioxane film former is Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000.

When the film forming resin is made up predominantly of trifunctional $RSiO_{3/2}$ units or T units, wherein R is a propyl radical, it is called a polypropylsilsesquioxane.

One example of a polypropylsilsesquioxane resin suitable for use in the present invention is commercially available from Dow-Corning as Dow Corning 670 Fluid. Dow Corning 670 Fluid has a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight.

A particularly preferred film-forming polymer for use in the present invention is a polypropylsilsesquioxane resin.

The film-forming polymer is present in an amount generally ranging from about 5% to about 60% by weight, preferably from about 10% to about 50% by weight, and more preferably from about 15% to about 40% by weight, based on the weight of the composition. For purposes of making the inventive compositions, the film-forming polymer is present in an amount ranging from about 5 to about 60% by weight, preferably from about 10 to about 50% by weight, and more preferably from about 15 to about 40% by weight, based on the weight of the second composition.

Film Former Solvent

The composition of the invention also contains at least one volatile solvent capable of solubilizing the film former.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
|---|---|---|
| Octyltrimethicone | 93 | 1.2 |
| Hexyltrimethicone | 79 | 1.2 |

TABLE 2-continued

| Compound | Flash Point (° C.) | Viscosity (cSt) |
|---|---|---|
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

The solvent for the film-forming polymer is employed in an amount ranging from about 5 to about 90% by weight, preferably from about 10 to about 80% by weight, and more preferably from about 20% to about 70% by weight, based on the weight of the composition. For purposes of making the inventive compositions, the solvent for the film-forming polymer is employed in an amount ranging from about 20 to about 90% by weight, preferably from about 30 to about 80% by weight, and more preferably from about 40% to about 70% by weight, based on the weight of the second composition.

Polyorganosiloxane-Containing Polymer

The compositions contain a polyorganosiloxane-containing polymer, which as used herein refers to a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions. The polyorganosiloxane is preferably present in the compositions due to its excellent pay-off properties, and because it provides additional structuring properties.

The polyorganosiloxane-containing polymers may comprise at least one moiety corresponding to formula (I):

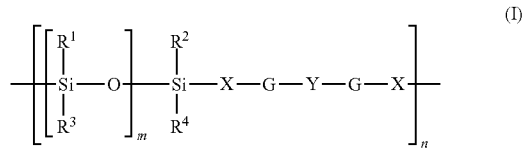

in which:
1) $R^1$, $R^2$, $R^3$ and $R^4$, which may be identical or different, represent a group chosen from:
   (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   (b) $C_6$ to $C_{10}$ aryl groups, optionally substituted with one or more $C_1$ to $C_4$ alkyl groups,
   (c) polyorganosiloxane chains possibly containing one or more oxygen, sulphur and/or nitrogen atoms;
2) X, which may be identical or different, represents a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;
4) G, which may be identical or different, represents a group chosen from ester, amide, sulphonamide, carbamate, thiocarbamate, urea, thiourea groups, and combinations thereof;
5) m is an integer ranging from 1 to 1,000, preferably from 1 to 700 and more preferably from 6 to 200; and
6) n is an integer ranging from 2 to 500 and preferably from 2 to 200.

The polyorganosiloxane-containing polymers may also comprise at least one moiety corresponding to formula (II):

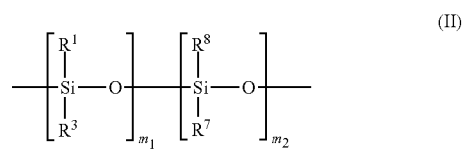

in which $R^1$ and $R^3$, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from 0, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

According to another embodiment, it is also possible to use a copolymer comprising several different moieties of formula (I), and/or several different moieties of formula (II), that is to say a polymer in which at least one of the groups $R^1$, $R^2$, $R^3$, $R^4$, X, G, Y, m and n is different in one of the moieties.

It is also possible to use a copolymer comprising at least one moiety of formula (I) and at least one moiety of formula (II), the moieties of formula (I) and the moieties of formula (II) possibly being identical to, or different from, each other. These copolymers may be block copolymers or grafted copolymers.

Additional polyorganosiloxane-containing polymers which may be used in the composition of the invention include those described in documents U.S. Pat. Nos. 5,874,069; 5,919,441; 6,051,216; and 5,981,680, the entire contents of which are hereby incorporated by reference.

A preferred polyorganosiloxane-containing polymer for use in the present invention will have at least one moiety chosen from formula (III):

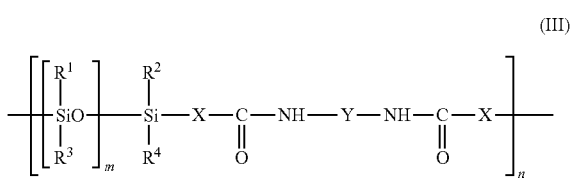

(III)

and formula (IV)

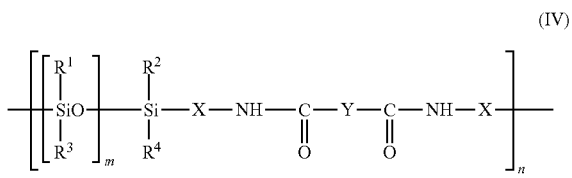

(IV)

in which:
(a) $R^1$, $R^2$, $R^3$ and $R^4$ are the same or different and may be selected from the group consisting of methyl, ethyl, propyl, isopropyl, a siloxane chain, and phenyl;
(b) X is a linear or branched chain alkylene having 1-30 carbons;
(c) Y is selected from the group consisting of linear or branched chain alkylenes having 1-40 carbons;
(d) m is a number between 1 and 700;
(e) n is a number between 1 and 500.

Particularly preferred polyorganosiloxane-containing polymers useful herein are commercially available from Dow Corning as DC 8178 and DC 8179, which are known under the INCI denomination of Nylon-611/Dimethicone Copolymer.

The polyorganosiloxane-containing polymer is present in an amount generally ranging from about 1 to about 10% by weight, such as from about 2 to about 8% by weight, and from about 3 to about 6% by weight, all weights being based on the total weight of the composition.

For purposes of making the inventive compositions, the polyorganosiloxane-containing polymer can be present in the composition according to the invention in an amount of from 1 to 30% by weight, preferably from 2 to 20% by weight, preferably from 3 to 10% by weight, based on the total weight of the second composition.

Colorant

Suitable colorants for use in the present invention include, for example, pigments and lakes. The precise amount and type to be used will depend on the composition's ultimate intended use and can be easily determined by those skilled in the art of cosmetic formulation. Typically, to make a composition that is non-transparent and thus colored in appearance, the amount of colorant will be greater than about 0.5% by weight of the composition. Inventive compositions that are transparent contain colorant but in an amount less than about 0.5% by weight.

The composition may also contain, if desired, at least one other type of active ingredient. Examples of suitable active ingredients include, for example, dermatological ingredients such as sunscreen agents, anti-acne agents, anti-aging compounds; insect repelling agents; transdermal pharmaceutical compounds; perfumes; dye compounds; etc.

The active ingredient (e.g., colorant) is present in amounts generally ranging from about 0.01 to 20 wt % and in some embodiments from about 0.1 to about 10% by weight, based on the total weight of the composition.

The compositions should be stable under conventional storage conditions. In order to achieve storage stability, the composition must have a melting point of about 50° C. or higher, such as 70° C. or higher, and 100° C. or higher.

The compositions should also have good "pay-off", i.e., the ability to be elegantly and uniformly deposited onto a targeted substrate. This property is dependent on the hardness of the composition. The hardness of the composition may, for example, be expressed in gramforce (gf). The composition of the present invention may, for example, have a hardness ranging from about 30 gf to about 300 gf, such as from about 50 gf to about 120 gf, and further such as from about 60 gf to about 100 gf.

Hardness is measured in one of two ways. A first test for hardness entails penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is known as the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value obtained from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on a targeted substrate. In addition, this hardness may impart good impact strength to the inventive compositions, which may be molded, cast, or extruded, for example, in stick or dish form.

The compositions may be used as a lip gloss, mascara, a hair styling composition, deodorant, foundation, and the like.

The present invention will be better understood from the examples which follow, all of which are intended for illustrative purposes only, and are not meant to unduly limit the scope of the invention in any way.

EXAMPLES

Long wear and shine mascara, eye shadow or eye liner formulation.

| Phase | INCI Name | Ex 1 | Ex 2 | Ex 3 |
|---|---|---|---|---|
| A | PROPYLENE GLYCOL | 5 | 5 | 0 |
| A | ISOSTEARYL ALCOHOL | 0 | 0 | 10 |
| A | dibutyl lauroyl glutamide (GP-1) | 3 | 4 | 4.66 |
| A | Dibutyl ethylhexanoyl glutamide EB-21 | 2 | 2 | 2.33 |
| B | Tpropyl silsesquioxane in Cyclopentasiloxane | 30 | 30 | 30 |

-continued

| Phase | INCI Name | Ex 1 | Ex 2 | Ex 3 |
|---|---|---|---|---|
| B | Cyclopentasiloxane | 48 | 47 | 40 |
| C | Pigments | 12 | 12 | 12 |
|   | TOTAL | 100 | 100 | 100 |

Procedure:

1. Heated propylene glycol or isostearyl alcohol to around 100° C., then added gelators GP-1 and EB-21 gradually during mixing until they were dissolved to form a clear solution.
2. In the other beaker, phase B was prepared by heating the oils to 90° C. and then dissolved the T-propyl silsesquioxane.
3. Once both phases were homogenous, combined and mixed the two. Poured the beaker component B into beaker component A at temperature of 90° C. and mixed until it became homogeneous.
4. Pigments in phase C was added and mixed.
5. Poured the hot solution into the mold. Once the solution set in the mold, put the mold in the freezer for about 30 minutes. The resultant product was a Stick in hard gel form.

Example 2

Foundation Gel Stick

| Phase | INCI Name | Ex 1 |
|---|---|---|
| A | Pentylene Glycol | 5 |
| A | dibutyl lauroyl glutamide. (GP-1) | 2 |
| A | dibutyl ethylhexanoyl glutamide. (EB-21) | 3 |
| B | Bis-hydroxyethoxypropyl Dimethicone (CARBINOL FLUID) | 20 |
| B | Octododecanol | 10 |
| B | Dimethicone (5 cst) | 10 |
| B | cyclopentasiloxane | 26 |
| B | Tpropyl silsesquioxane in Cyclopentasiloxane (50% solid) | 10 |
| B | NYLON-611/DIMETHICONE COPOLYMER | 2 |
| C | Pigments | 12 |
|   | TOTAL | 100 |

Procedure:

1. Heated pentylene glycol to around 100° C., then added gelators GP-1 and EB-21 gradually during mixing until they were dissolved to form a clear solution.
2. In the other beaker, phase B was prepared by heating the oils to 90° C. and then dissolved with the Nylon-611/dimethicone copolymer.
3. Once both phases were homogenous, combined and mixed the two. Poured the beaker component B into beaker component A at temperature of 90° C. and mixed until it became homogeneous.
4. Pigments in phase C were added and mixed.
5. Poured the hot solution into the mold. Once the solution set in the mold, placed the mold in the freezer for about 30 minutes. The resultant product was a stick in hard gel form.

Example 3

Mascara Gel Stick

| Phase | INCI Name | Ex 2 |
|---|---|---|
| A | Pentylene Glycol | 5 |
| A | dibutyl lauroyl glutamide (GP-1) | 3 |
| A | dibutyl ethylhexanoyl glutamide (EB-21) | 2 |
| B | Bis-hydroxyethoxypropyl Dimethicone (CARBINOL FLUID) | 20 |
| B | Octododecanol | 10 |
| B | cyclopentasiloxane | 38 |
| B | Tpropyl silsesquioxane in Cyclopentasiloxane (50% solid) | 10 |
| B | NYLON-611/DIMETHICONE COPOLYMER | 2 |
| C | Iron oxides | 10 |
|   | TOTAL | 100 |

Procedure: Same Procedure as Above for Example 2.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A non-aqueous composition that is capable of forming a gel structure, comprising:
    a structuring agent consisting of: (a) a low molecular mass N-acyl glutamic acid diamide having a straight-chain alkyl group comprising dibutyl lauroyl glutamide; (b) a low molecular mass N-acyl glutamic acid diamide having a branched-chain alkyl group comprising dibutyl ethylhexanoyl glutamide; and (c) at least one polyorganosiloxane polymer comprising a nylon-611/dimethicone copolymer:
    (d) at least one gel-promoting solvent;
    (e) at least one film former;
    (f) at least one volatile solvent capable of solubilizing the film former; and
    (g) at least one colorant;
    wherein the composition has a hardness value ranging from about 30 to about 300gf, a melting point of about 50° C. or higher.

2. The composition of claim 1 wherein (a) is employed in an amount of from about 0.1 to about 10% by weight, based on the weight of the composition.

3. The composition of claim 1 wherein (b) is employed in an amount of from about 0.1 to about 10% by weight, based on the weight of the composition.

4. The composition of claim 1 wherein (d) is chosen from a C2-C5 glycol, isostearyl alcohol, and mixtures thereof.

5. The composition of claim 1 wherein (d) is employed in an amount of from about 3 to about 20% by weight, based on the weight of the composition.

6. The composition of claim 1 wherein (e) is t-propylsilsesquioxane.

7. The composition of claim 1 wherein (e) is employed in an amount of from about 5 to about 60% by weight, based on the weight of the composition.

8. The composition of claim 1 wherein (f) is cylcopentasiloxane.

9. The composition of claim 1 wherein (f) is employed in an amount of from about 5 to about 90% by weight, based on the weight of the composition.

10. A process for making a non-aqueous composition that is capable of forming a gel structure, comprising:
   providing a structuring agent consisting of: (a) a low molecular mass N-acyl glutamic acid diamide having a straight-chain alkyl group comprising dibutyl lauroyl glutamide;
   (b) a low molecular mass N-acyl glutamic acid diamide having a branched-chain alkyl group comprising dibutyl ethylhexanoyl glutamide; and (c) and at least one polyorganosiloxane polymer comprising a nylon-611/dimethicone copolymer;
   (d) providing at least one gel-promoting solvent;
   (e) providing at least one film former;
   (f) providing at least one volatile solvent capable of solubilizing the film former; and
   (g) providing at least one colorant; and
   (h) mixing (a)-(g), at a temperature of from about 80° C. to about 125° C., to form a heated composition; and (i) cooling the heated composition to form the non-aqueous, structured, gel-form composition, wherein the composition has a hardness value ranging from about 30 to about 300gf, a melting point of about 50° C. or higher.

11. The process of claim 10, which comprises: a) providing a first composition, comprising: i) the low molecular mass N-acyl glutamic acid diamide having a straight-chain alkyl group; ii) the low molecular mass N-acyl glutamic acid diamide having a branched-chain alkyl group; and
   iii) the at least one gel-promoting solvent; b) providing a second composition, comprising: (i) the at least one film former; ii) the at least one volatile solvent; iii) the at least one colorant; and iv) the at least one polyorganosiloxane-containing polymer; c) mixing (a) and (b) at a temperature of from about 90° C. to about 125° C., to form a heated composition; and d) cooling the heated composition to form the non-aqueous composition.

* * * * *